United States Patent
Pinchasik

(10) Patent No.: US 6,689,123 B2
(45) Date of Patent: *Feb. 10, 2004

(54) APPARATUS AND METHOD FOR SECURING A STENT ON A BALLOON

(75) Inventor: Gregory Pinchasik, Herzlia (IL)

(73) Assignee: Medinol Ltd., Tel-Aviv (IL)

( * ) Notice: Subject to any disclaimer, the term of this patent is extended or adjusted under 35 U.S.C. 154(b) by 148 days.

This patent is subject to a terminal disclaimer.

(21) Appl. No.: 10/045,262

(22) Filed: Nov. 7, 2001

(65) Prior Publication Data

US 2002/0107507 A1 Aug. 8, 2002

Related U.S. Application Data

(63) Continuation of application No. 09/360,415, filed on Jul. 23, 1999, now Pat. No. 6,364,870, and a continuation of application No. 09/218,503, filed on Dec. 22, 1998, now abandoned.

(51) Int. Cl.[7] .............................................. A61B 17/00
(52) U.S. Cl. ........................................ 606/1; 623/909
(58) Field of Search .......................... 606/1, 108, 198; 29/516, 235, 270, 407.01, 282, 283.5; 72/409.19, 402, 410, 466.8, 416; 425/517; 623/1.11, 1.12, 1.23, 901, 909

(56) References Cited

U.S. PATENT DOCUMENTS

| | | | |
|---|---|---|---|
| 3,575,036 A | * | 4/1971 | Hoffman et al. ............... 72/402 |
| 5,183,085 A | | 2/1993 | Timmermans |
| 5,353,623 A | | 10/1994 | Bobenhausen |
| 5,546,646 A | | 8/1996 | Williams et al. |
| 5,630,830 A | | 5/1997 | Verbeek |
| 5,672,169 A | | 9/1997 | Verbeek |
| 5,720,197 A | * | 2/1998 | Grau et al. ................... 72/402 |
| 5,725,519 A | | 3/1998 | Penner et al. |
| 5,810,838 A | | 9/1998 | Solar |
| 5,893,867 A | | 4/1999 | Bagaoisan et al. |
| 5,893,868 A | | 4/1999 | Hanson et al. |
| 5,931,851 A | | 8/1999 | Morales |
| 5,951,540 A | | 9/1999 | Verbeek |
| 5,992,000 A | | 11/1999 | Humphrey et al. |
| 6,009,614 A | | 1/2000 | Morales |
| 6,024,737 A | | 2/2000 | Morales |
| 6,364,870 B1 | * | 4/2002 | Pinchasik ..................... 606/1 |

FOREIGN PATENT DOCUMENTS

| | | |
|---|---|---|
| DE | 195 32 288 | 3/1997 |
| WO | 97/20593 | 6/1997 |

* cited by examiner

*Primary Examiner*—Eduardo C. Robert
(74) *Attorney, Agent, or Firm*—Kenyon & Kenyon

(57) ABSTRACT

Apparatus and method for securing a stent to a balloon catheter. A first clamping portion and a second clamping portion are arranged for movement toward and away from each other and are provided with recesses defining a channel to receive a stent crimping sleeve having a longitudinal bore. The stent is slid into the longitudinal bore of the stent crimping sleeve and the balloon catheter is then slid into the longitudinal bore of the stent. The first and second clamping portions are moved towards each other and apply pressure to the external surface of the stent crimping sleeve causing the internal diameter of the longitudinal bore to get smaller and apply pressure to the external surface of the stent and crimp the stent to the balloon.

9 Claims, 8 Drawing Sheets

APPARATUS AND METHOD FOR SECURING A STENT ON A BALLOON

This application is a continuation of U.S. patent application Ser. No. 09/218,503 filed Dec. 22, 1998 (now abandoned), and Ser. No. 09/360,415 filed Jul. 23, 1999, now U.S. Pat. No. 6,364,870.

FIELD OF THE INVENTION

The present invention relates generally to intravascular stents for implanting into a living body. In particular, the present invention relates to intravascular stents that are expanded by an inflatable balloon catheter and to a method and apparatus for mounting and securing a stent on a balloon catheter.

BACKGROUND OF THE INVENTION

Intravascular stents having a constricted diameter for delivery through a blood vessel and an expanded diameter for applying a radially outwardly extending force for supporting the blood vessel are known in the art. Selfexpandable articulated stents are described, for example, in U.S. Pat. No. 5,104,404, entitled "Articulated Stent" to Wolff. Balloon expandable articulated stents are commercially available under the trade name Palmaz-Schatz Balloon-Expandable stents from Johnson & Johnson International Systems Co.

In conventional stent mounting and securing procedures, the stent is usually first slid over the distal end of a balloon catheter so that the expandable balloon is disposed within the longitudinal bore of the stent. The stent is then crimped or pinched to mount or secure the stent and maintain its position with respect to the expandable balloon as the balloon catheter is advanced to the target area. This crimping is often done utilizing the fingers or a plier-like device to pinch the stent. One shortcoming of this conventional mounting and securing means is that it often produces irregular distortion of the stent which could cause trauma to the lumen being treated. Another shortcoming is that it may weaken a portion or portions of the stent which could result in stent failure. Yet another shortcoming of conventional mounting and securing methods is that they may distort the stent in such a way as to cause the stent to expand in the target area in a non-uniform manner which could result in a portion of the lumen not being properly supported.

Yet another shortcoming of conventional mounting and securing methods is irregular distortion of the stent could produce protrusions in the stent which could cause trauma to the patient.

Therefore, it would be highly desirable to have a method and an apparatus that permits a stent to be secured over the expandable balloon of a balloon catheter without causing irregular distortion or weakening the stent.

OBJECTS AND SUMMARY OF THE INVENTION

It is an object of this invention to provide an apparatus for securing a stent on a balloon catheter by substantially uniformly distorting the stent.

It is another object of this invention to provide an apparatus for securing a stent on a balloon catheter that reduces the likelihood that the stent will expand in a nonuniform manner.

It is yet another object of this invention to provide a method of securing a stent on a balloon catheter that reduces the likelihood that the stent will be weakened by the securing procedure.

It is a further object of this invention to provide an apparatus for securing a stent on a balloon catheter, comprising:

a) a first clamping portion provided with a first clamping portion recess, said first clamping portion recess sized and adapted to receive a stent crimping sleeve;

b) a second clamping portion provided with a second clamping portion recess, said second clamping portion recess sized and adapted to receive a stent crimping sleeve, said first clamping portion recess and said second clamping portion recess defining a longitudinal stent crimping sleeve channel having a variable cross-sectional diameter, said first and said second clamping portions adapted for movement in a first direction away from each other to a first position and in a second direction toward each other to a second position to selectively impart pressure to a stent crimping sleeve disposed in said longitudinal stent crimping sleeve channel, said clamping portion recesses sized and adapted so that said longitudinal stent crimping sleeve channel has a substantially circular cross-sectional diameter when said first and said second clamping portions are in said second position;

c) a stent crimping sleeve disposed in said crimping sleeve channel, said sleeve having a first end, a second end, an outer surface, and an inner surface defining a longitudinal stent crimping bore therethrough, said longitudinal stent crimping bore having a selectively variable-substantially circular cross-sectional diameter and sized and adapted to receive a balloon catheter with a stent mounted thereon, said stent crimping sleeve further adapted to selectively and substantially uniformly vary said substantially circular cross-sectional diameter of said longitudinal stent crimping bore in response to pressure applied to said external surface of said stent crimping sleeve by said first clamping portion and said second clamping portion when said first clamping portion and said second clamping portion are moved in said second direction.

It is still another object of this invention to provide a method of securing an expandable stent having a longitudinal bore on a balloon catheter, comprising the steps of:

a) constructing an apparatus comprising: a first clamping portion provided with a first clamping portion recess, said first clamping portion recess sized and adapted to receive a stent crimping sleeve; a second clamping portion provided with a second clamping portion recess, said second clamping portion recess sized and adapted to receive a stent crimping sleeve, said first clamping portion recess and said second clamping portion recess defining a longitudinal stent crimping sleeve channel having a variable cross-sectional diameter, said first and said second clamping portions adapted for movement in a first direction away from each other to a first position and in a second direction toward each other to a second position to selectively impart pressure to a stent crimping sleeve disposed in said longitudinal stent crimping sleeve channel, said clamping portion recesses sized and adapted so that said longitudinal stent crimping sleeve channel has a substantially circular cross-sectional diameter when said first and said second clamping portions are in said second position; a stent crimping sleeve having a first end, a second end, an outer surface, and an inner surface defining a longitudinal stent crimping bore therethrough having a selectively variable substantially circular cross-sectional diameter and sized and adapted to receive a balloon catheter with a stent mounted thereon, said stent crimping sleeve further adapted to selectively and substantially uniformly vary said substantially circular cross-sectional diameter of said longitudinal stent crimping bore in response to pressure applied to said external surface of said stent crimping sleeve by said first clamping portion and said second clamping portion;

b) disposing said stent crimping sleeve in said stent crimping sleeve channel;

c) disposing said stent in said longitudinal stent crimping bore of said stent crimping sleeve;

d) disposing said balloon catheter in said longitudinal bore of said stent; and e) moving said first and said second stent clamping portions from said first position to said second position so as to apply pressure to said external surface of said stent crimping sleeve in an amount sufficient to decrease the substantially circular cross-sectional diameter of said longitudinal stent crimping bore in an amount sufficient for said inner surface of said stent crimping sleeve to impart sufficient pressure to said stent to secure said stent to said balloon catheter.

It is a further object of this invention to provide an apparatus for securing a stent on a balloon catheter, comprising:

a) a first clamping portion having a first clamping portion recess and a second clamping portion having a second clamping portion recess, said first and said second clamping portion recesses defining a longitudinal stent crimping element channel with a variable cross-sectional diameter, said first and said second clamping portions adapted for movement in a first direction away from each other to a first position and in a second direction toward each other to a second position;

b) a plurality of crimping elements disposed within said longitudinal stent crimping element channel defining a stent crimping sleeve channel having a variable cross-sectional diameter, said plurality of crimping elements adapted for movement in a first direction away from each other to a first position and in a second direction toward each other to a second position; and c) a stent crimping sleeve disposed in said longitudinal stent crimping sleeve channel, having a first end, a second end, an outer wall, and an inner wall defining a longitudinal bore therethrough having a selectively variable substantially circular crosssectional diameter, said clamping portions said crimping elements, and said sleeve adapted and disposed so that when said first clamping portion, said second clamping portion, and said plurality of crimping elements are disposed in the second position, said crimping elements define a longitudinal stent crimping sleeve channel having a substantially circular crosssectional diameter and said longitudinal stent crimping bore defines a longitudinal bore having a substantially circular crosssectional diameter.

It is a yet another object of this invention to provide an apparatus for securing a stent on a balloon catheter, comprising:

a) a first clamping portion and a second clamping portion, said first clamping portion provided with a first surface, a second surface and a third surface defining a first clamping portion recess, said second clamping portion provided with a first surface, a second surface, a third surface, a fourth surface and a fifth surface defining a second clamping portion recess, said first and said second clamping portion recesses defining a longitudinal stent crimping element channel with a variable diameter, said first and said second clamping portions adapted for movement in a first direction away from each other to a first position and in a second direction toward each other to a second position;

b) a first crimping element disposed within said longitudinal stent crimping element channel said first crimping element provided with a first crimping element contact surface, a second crimping element contact surface, a first clamping portion contact surface, and a stent crimping sleeve contact surface;

c) a second crimping element disposed within said longitudinal stent crimping channel, said second crimping element provided with a first crimping element contact surface, a second crimping element contact surface, a first clamping portion contact surface, and a stent crimping sleeve contact surface;

d) a third crimping element disposed within said longitudinal stent crimping channel, said third crimping element provided with a first crimping element contact surface, a second crimping element contact surface, a second clamping portion contact surface, and a stent crimping sleeve contact surface;

e) a fourth crimping element disposed within said longitudinal stent crimping channel, said fourth crimping element provided with a first crimping element contact surface, a second crimping element contact surface, a second clamping portion contact surface, and a stent crimping sleeve contact surface, said crimping elements adapted for movement in a first direction away from each other to a first position and in a second direction towards each other to a second position, said stent crimping sleeve contact surfaces defining a stent crimping sleeve channel having a variable cross-sectional diameter that is substantially circular-when said plurality of crimping elements are disposed in said second position; and f) a stent crimping sleeve disposed in said longitudinal stent crimping sleeve channel, said sleeve having a first end, a second end, an outer wall, and an inner wall defining a longitudinal bore therethrough having a selectively variable substantially circular crosssectional diameter, said clamping portions, said crimping elements, and said sleeve adapted and disposed so that when said first clamping portion and said second clamping portion are in the second position, said crimping sleeve contact surfaces define a stent crimping sleeve channel having a substantially circular crosssectional diameter and said longitudinal bore defines a longitudinal bore having a substantially circular cross-sectional diameter.

DETAILED DESCRIPTION OF THE INVENTION

Figure 1:
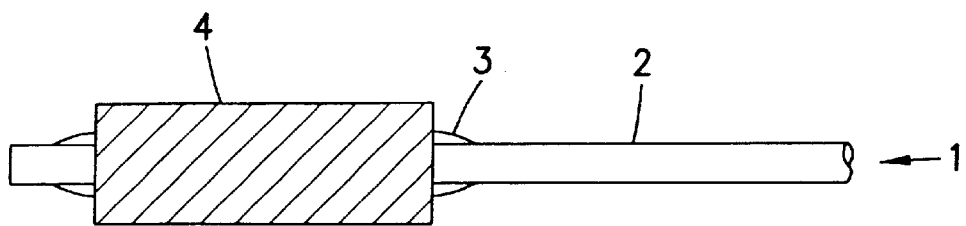
FIG. 1 is a side view of a stent placed on a balloon catheter before the stent has been secured to the balloon.
Figure 2:
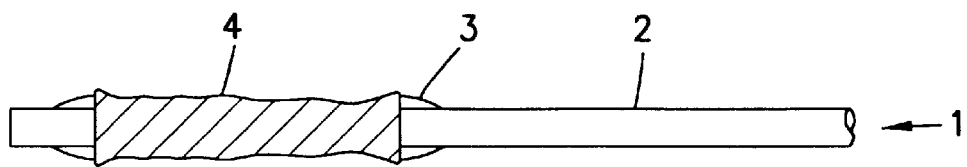
FIG. 2 is a side view of the stent of FIG. 1 after the stent has been secured to the balloon utilizing conventional securing methods.

FIG. 1 shows a conventional balloon catheter 1 and shows a catheter 2, a balloon 3, and a stent 4 mounted on the balloon 3 prior to the stent 4 being secured on the balloon 3. FIG. 2 shows the stent of FIG. 1 after it has been secured to the balloon by conventional methods, e.g., by pinching between the fingers or by crimping with a conventional plier-like device. As shown in FIG. 2, the ends of the stent protrude and there is some irregular distortion of the stent between the two ends of the stent.

Figure 4:
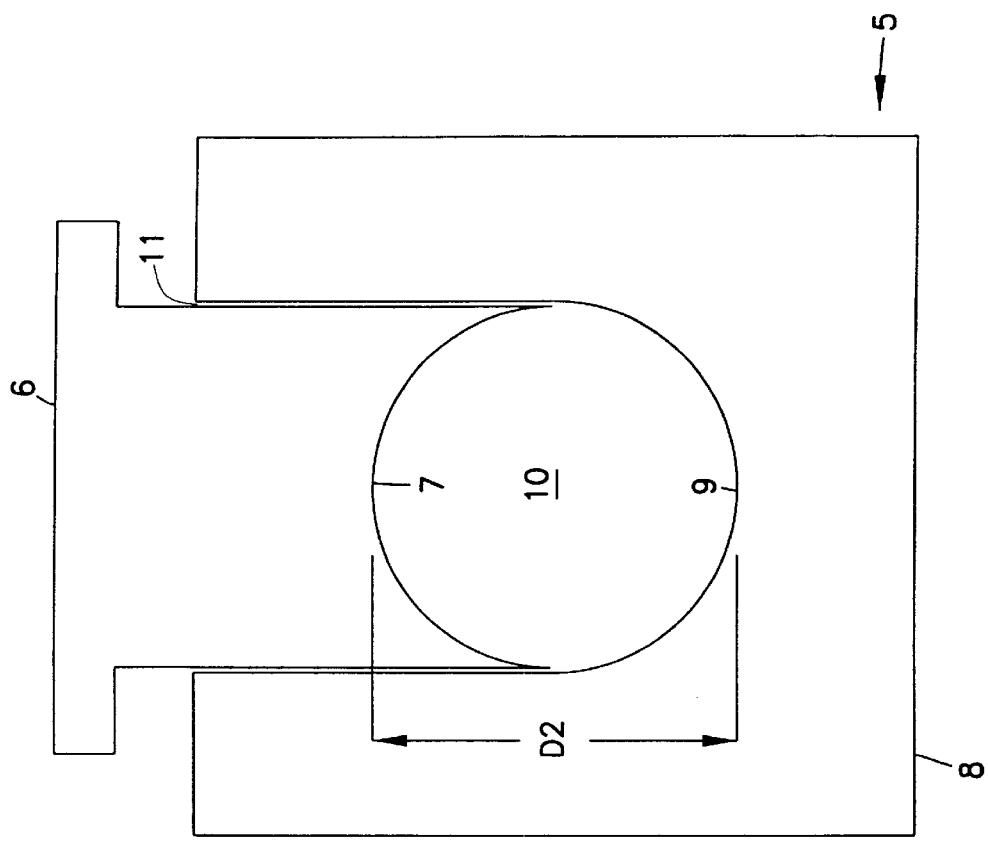
FIG. 4 is a cross-sectional end view of a stent securing apparatus constructed in accordance with this invention with the clamping portions disposed in a second or securing position.
Figure 3:
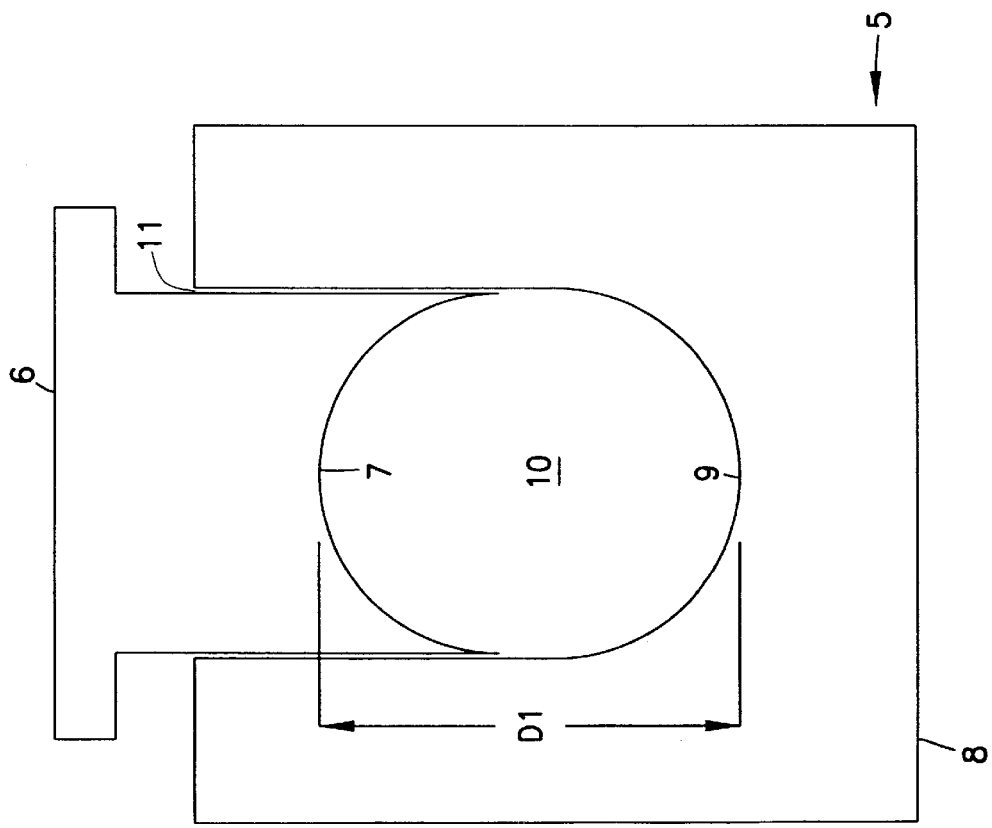
FIG. 3 is a cross-sectional end view of a stent securing apparatus constructed in accordance with this invention with the clamping portions disposed in a first or non-securing position.

FIG. 3 shows a stent securing apparatus 5 constructed in accordance with the invention. FIG. 3 shows a first clamping portion 6 having a first clamping portion recess 7 and a second clamping portion 8 having a second clamping portion recess 9. The first clamping portion recess 7 and the second clamping portion recess 9 define a longitudinal stent crimping sleeve channel 10 with a selectively variable cross-sectional diameter. FIG. 3 shows the first clamping portion 6 and the second clamping portion 8 disposed in a first or non-securing position which provides a first clearance D1 between the first clamping portion 6 and the second clamping portion 8 that is adequate for inserting an uncompressed stent crimping sleeve into the stent crimping sleeve channel 10. FIG. 4 shows the first clamping portion 6 and the second clamping portion 8 of FIG. 3 moved to a second or securing position with a second clearance D2 between the first clamping portion 6 and the second clamping portion 8 that is less than that D1. Thus, when disposed in the second or securing position, the first clamping portion 6 and the second clamping portion 8 are closer to each other than they are when disposed in the first position and, as shown in FIGS. 3 and 4, the crimping sleeve channel 10 has a smaller diameter. As also shown in FIG. 4, when the first clamping portion 6 and the second clamping portion 8 are in the second position, the crimping sleeve channel 10 has a substantially circular crosssectional diameter. The first clamping portion 6 and the second clamping portion 8 may be arranged in a variety of ways well known to those skilled in the art which permits selective movement of the first clamping portion 6 and second clamping portion 8 from the first position to the second position, i.e., toward and away from each other. In the embodiment shown, a channel 11 aligns the first clamping portion 6 and second clamping portion 8 and external pressure, e.g., finger pressure may be utilized to move the first clamping portion 6 and 8 from the first position to the second position. In another embodiment, pneumatic pressure or an electrical motor is utilized to move the clamping portions 6 and 8. In an especially preferred embodiment, a pressure gauge and pressure regulator are utilized to control the amount of pressure applied. In still another embodiment, the first and second clamping portions 6 and 8 are mounted on a plier like hinged device.

Figure 5:
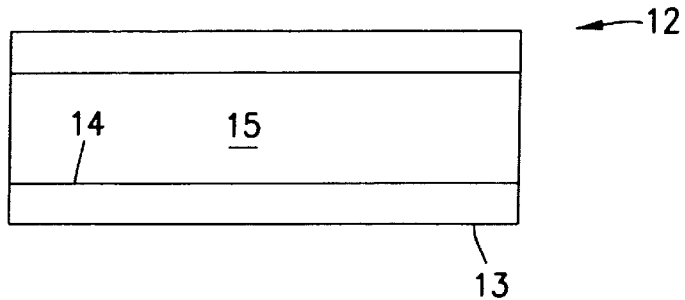
FIG. 5 is a cross-sectional side view of a stent crimping sleeve constructed in accordance with the invention.
Figure 6:
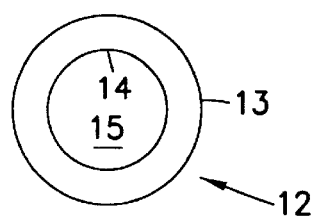
FIG. 6 is an end view of the stent crimping sleeve shown in FIG. 5.

FIG. 5 is a cross-sectional side view of a stent crimping sleeve 12 having an outer surface 13 and an inner surface 14 defining a longitudinal stent crimping bore 15. FIG. 6 is an end view of FIG. 5. The stent crimping bore 15 has a selectively variable substantially circular crosssectional diameter that changes in response to external pressure applied to the external surface 13 of the stent crimping sleeve 12. The material comprising the stent crimping sleeve 12 is selected from a material which will substantially uniformly vary and maintain the substantially circular cross-sectional diameter of the longitudinal stent crimping bore 15 in response to pressure applied to the outer surface 13 of the stent crimping sleeve 12. In a preferred embodiment, polyurethane is utilized.

Figure 7:
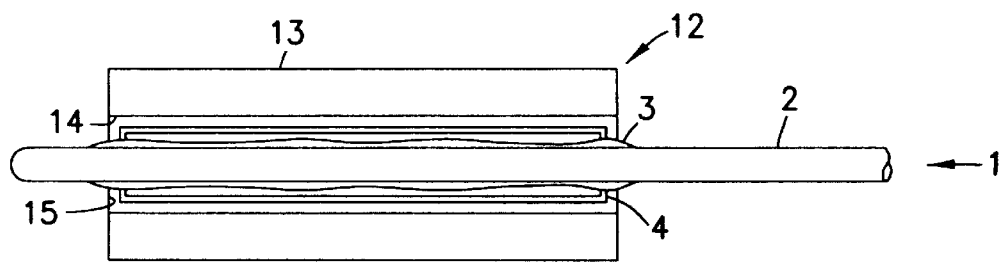
FIG. 7 is a cross-sectional side view of the stent crimping sleeve of FIGS. 5 and 6 with the balloon catheter and stent of FIG. 1 disposed within it prior to the stent being secured to the balloon.
Figure 8:
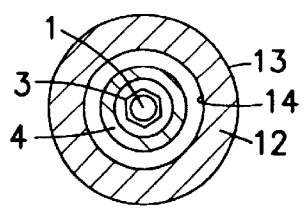
FIG. 8 is an end view of FIG. 7.

FIG. 7 shows the stent 4, balloon 3, and catheter 2 of FIG. 1 disposed within the longitudinal stent crimping bore 15 of the stent crimping sleeve 12 shown in FIG. 5 prior to the stent 4 being crimped and secured to the balloon 3. FIG. 8 is an end view of FIG. 7.

Figure 9:
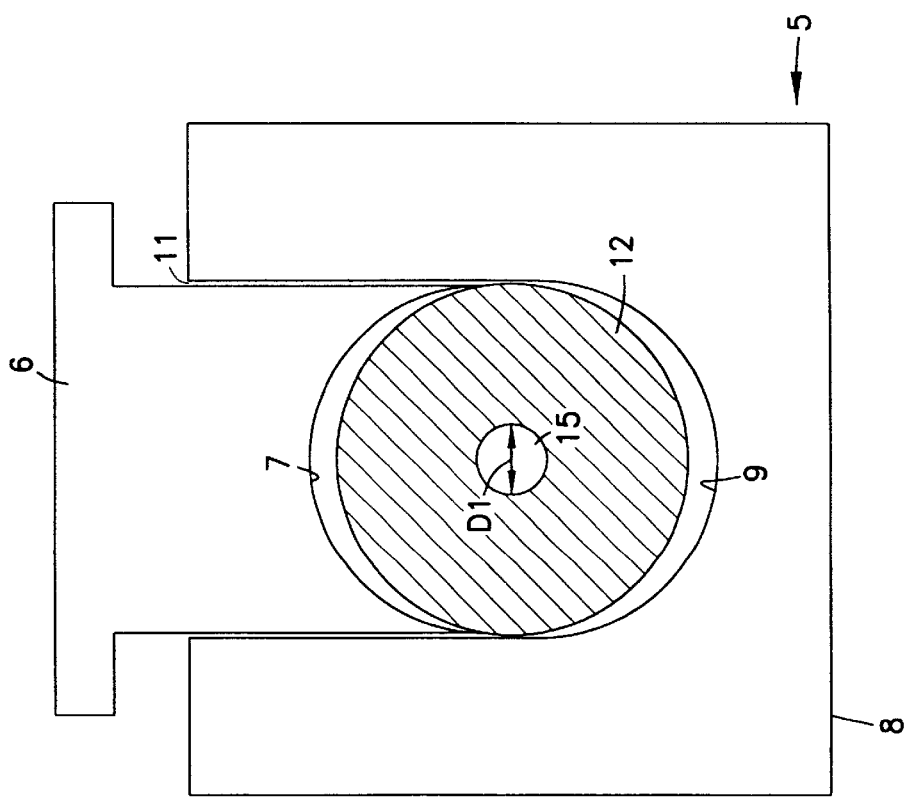
FIG. 9 shows the stent crimping sleeve shown in FIGS. 5 and 6 disposed between the first and second clamping portions with the first and second clamping portions disposed in a first or non-securing position.

FIG. 9 shows the stent crimping sleeve 12 of FIGS. 5 and 6 disposed in the stent crimping sleeve channel 10 between the first stent clamping portion 6 and second stent clamping portion 8 of the stent securing apparatus 5. As shown in FIG. 9, the first stent clamping portion 6 and second stent clamping portion 8 are disposed in a first position which provides adequate clearance in the stent crimping sleeve channel 10 for the stent crimping sleeve 12 to be easily inserted or removed from the stent crimping sleeve channel 10. Longitudinal bore 15 has a substantially circular cross-sectional diameter D1.

Figure 10:
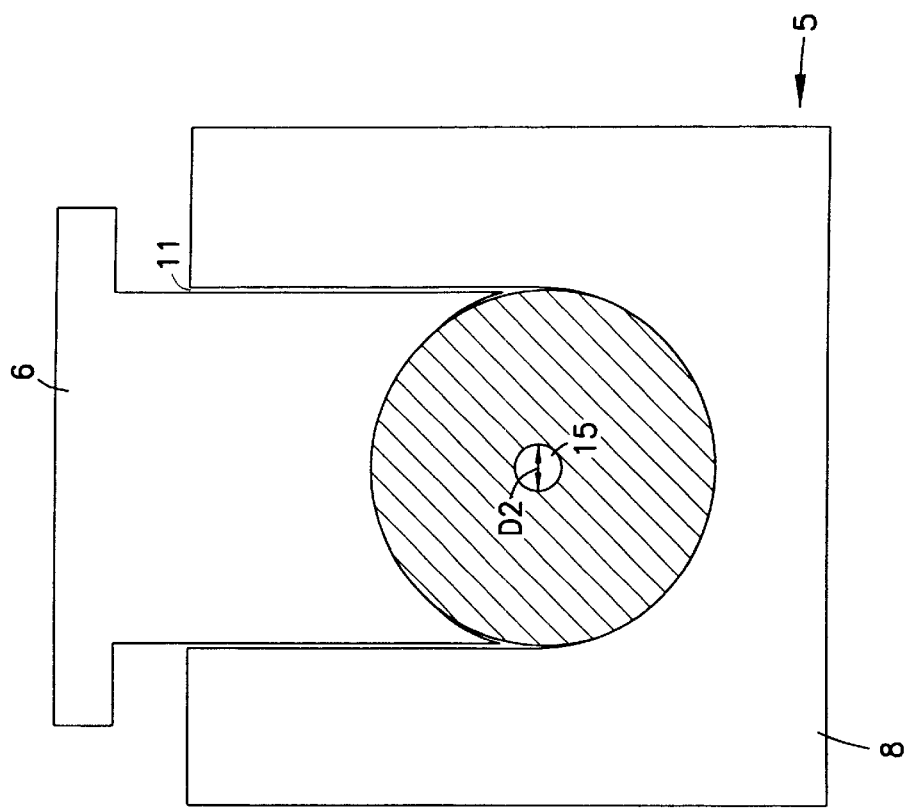
FIG. 10 shows the stent crimping sleeve shown on FIGS. 5 and 6 disposed between the first and second clamping portions with the first and second clamping portions moved to a second or securing position.

FIG. 10 differs from FIG. 9 in that the first stent clamping portion 6 and the second stent clamping portion 8 have been moved to a second position. The first clamping portion recess 7 and the second clamping portion recess are sized and cooperatively adapted so that when disposed in the second position the first and second clamping portions 6 and 8 define a channel 10 having a substantially circular cross-sectional diameter. As shown in FIG. 10, in response to the pressure applied by the first and second clamping portions 6 and 8 on the external wall 13 of the stent crimping sleeve 12, the stent crimping sleeve 12 is compressed. This causes the diameter of the longitudinal stent crimping bore 15 to be reduced substantially uniformly to a substantially circular crosssectional diameter D2 which is less than the uncompressed diameter D1 shown in FIG. 9. In response to the external pressure-applied to the outer surface 13, the inner surface 14 of the stent crimping bore 15 applies a substantially uniform pressure to the stent 4 in an amount sufficient so as to substantially uniformly crimp the stent 4 and secure it on the balloon 3 with minimal irregular distortion of the stent 4 because the longitudinal bore 15 maintains its substantially circular cross-sectional diameter when the stent crimping sleeve 12 is compressed and the diameter of the stent crimping bore 15 is reduced.

Figure 11:
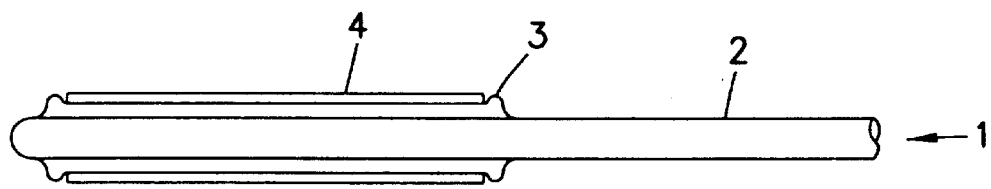
FIG. 11 shows the stent of FIG. 1 secured to the balloon catheter after being secured in accordance with the invention.

FIG. 11 is a side view of the stent shown in FIG. 1 after it has been secured in accordance with the invention and removed from the stent securing apparatus 5 and shows that the stent 4 has been substantially uniformly crimped and secured on the balloon 3 with minimal irregular distortion.

Figure 12:
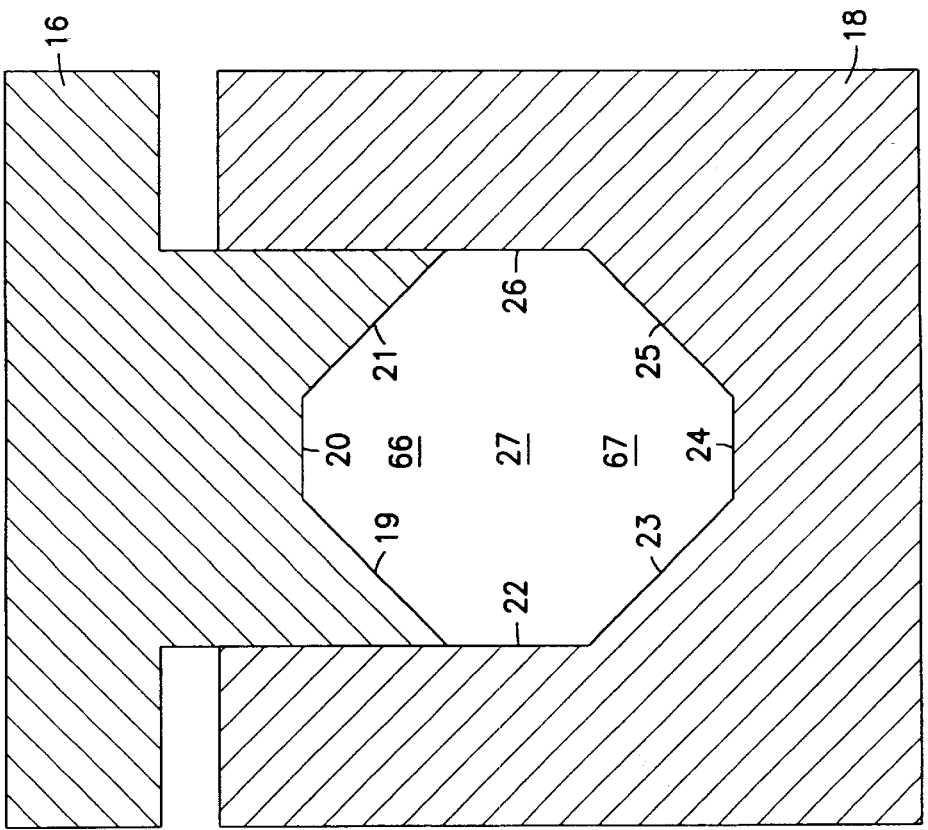
FIG. 12 shows an alternative embodiment of the invention having a first clamping portion and a second clamping portion disposed in a first position.

FIGS. 12 to 16 show an alternative embodiment of the invention that utilizes a plurality of crimping elements disposed between the clamping portions to apply pressure to a stent crimping sleeve. FIG. 12 shows a first clamping portion 16 and a second clamping portion 18. First clamping portion 16 is provided with a first surface 19, a second surface 20, and a third surface 21 defining a first clamping portion recess 66. Second clamping portion 18 is provided with a first surface 22, a second surface 23, a third surface 24, a fourth surface 25 and a fifth surface 26 defining a second clamping portion recess 67. The surfaces 19, 20, 21, comprising the first clamping portion recess 66 and the surfaces 22, 23, 24, 25, and 26 comprising the second clamping portion recess 67 define a longitudinal stent crimping element channel 27 with a selectively variable cross-sectional diameter.

Figure 13:
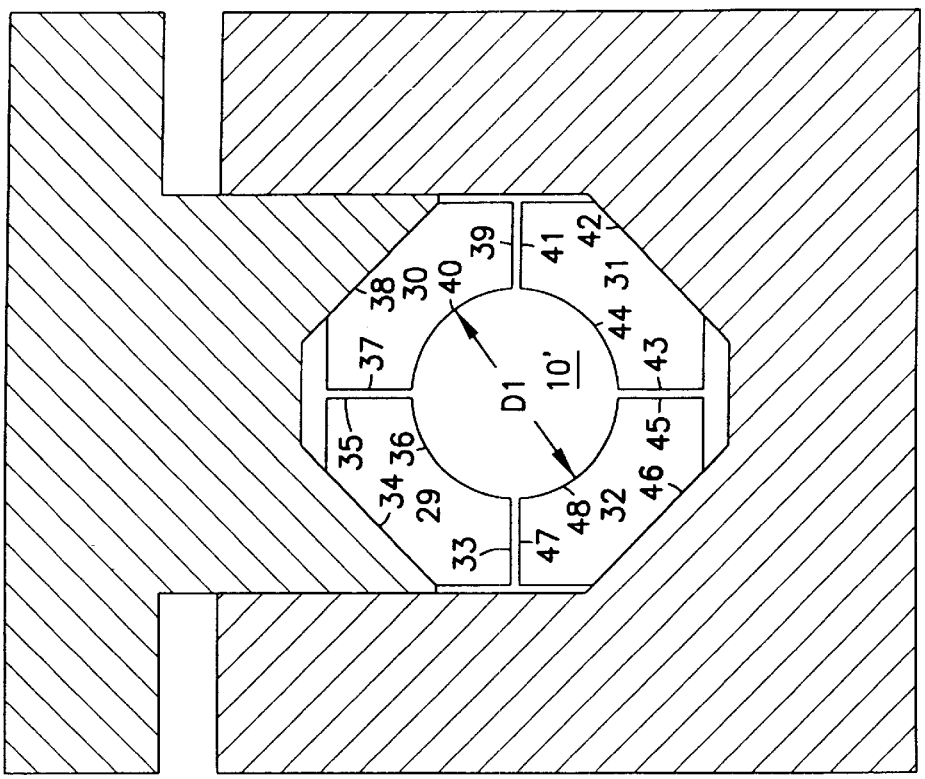
FIG. 13 shows the clamping portions shown in FIG. 12 with a plurality of crimping elements disposed between the clamping portions.

As shown in FIG. 13, disposed within the longitudinal stent crimping element channel 27 is a first crimping element 29, a second crimping element 30, a third crimping element 31 and a fourth crimping element 32. First crimping element 29 is provided with a first crimping element contact surface 33, a second crimping element contact surface 35, a first clamping portion contact surface 34 and a stent crimping sleeve contact surface 36. Second crimping element 30 comprises a first crimping element contact surface 37, a second crimping element contact surface 39, a first clamping portion contact surface 38 and a stent crimping sleeve contact surface 40. Third crimping element 31 is provided with a first crimping element contact surface 41, a second crimping element contact surface 43, a second clamping portion contact surface 42 and a stent crimping sleeve contact surface 44. Fourth crimping element 32 is provided with a first crimping element contact surface 45, a second crimping element contact surface 47, a second clamping portion contact surface 46, and a stent crimping sleeve contact surface 48. The stent crimping sleeve contact surfaces 36, 40, 44, and 48 define a stent crimping sleeve channel 10, having a selectively variable crosssectional diameter.

Figure 14:
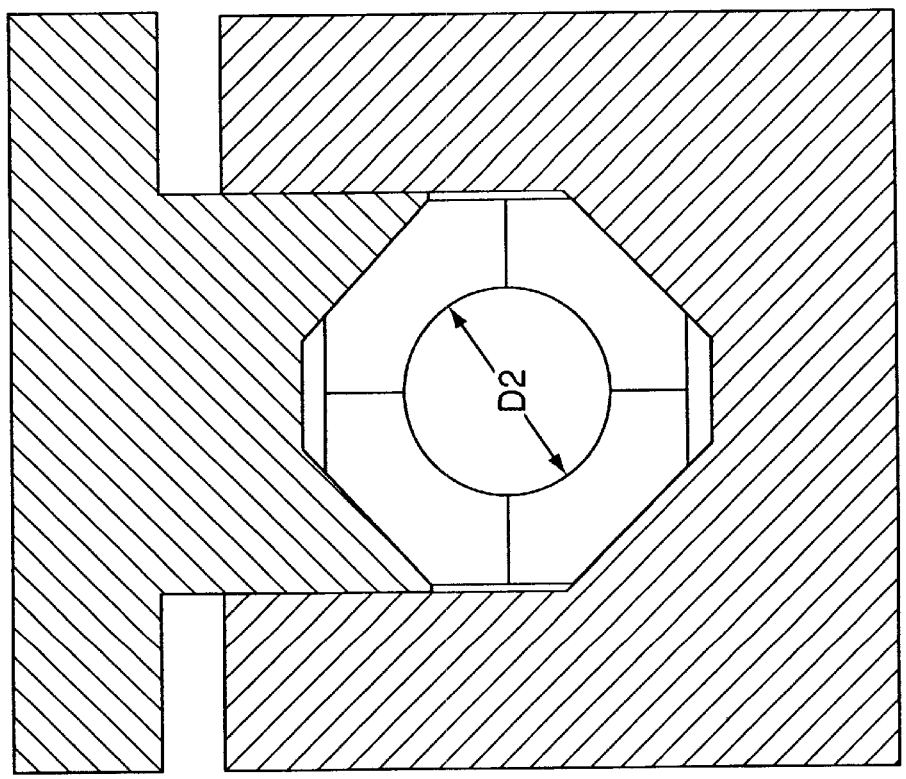
FIG. 14 shows the clamping portions and crimping elements of FIG. 13 disposed in a second position.

FIG. 13 shows the first clamping portion 16, the second clamping portion 18, and the crimping elements 29, 30, 31, and 32 disposed in a first or non-securing position, which provides a cross-sectional diameter D1 of the stent crimping sleeve channel 101 that is adequate for inserting an uncompressed stent crimping sleeve 12 into the stent crimping sleeve channel 101. As the first clamping portion 16 and the second clamping portion 18 are moved to the second position, surface 19 impinge on surface 34, surface 21 impinges upon surface 38, surface 23 impinges upon surface 46 and surface 25 impinges upon surface 42 moving the crimping elements 29, 30, 31, and 32 to a second or securing position. FIG. 14 shows the first clamping portion 16, the second clamping portion 18, and the crimping elements 29, 30, 31, and 32 disposed in a second position the stent crimping sleeve surfaces 36, 40, 44, and 48 define a crimping sleeve channel 10' having a substantially circular cross-sectional diameter D2 that is smaller than diameter D1 shown in FIG. 13. The first clamping portion 16 and second clamping portion 18 may be arranged in a variety of ways well skilled to those skilled in the art which permits selective movement of the first clamping portion 16 and second clamping portion 18 in a first direction away from each other to a first position and in a second direction toward each other to a second position.

Figure 15:
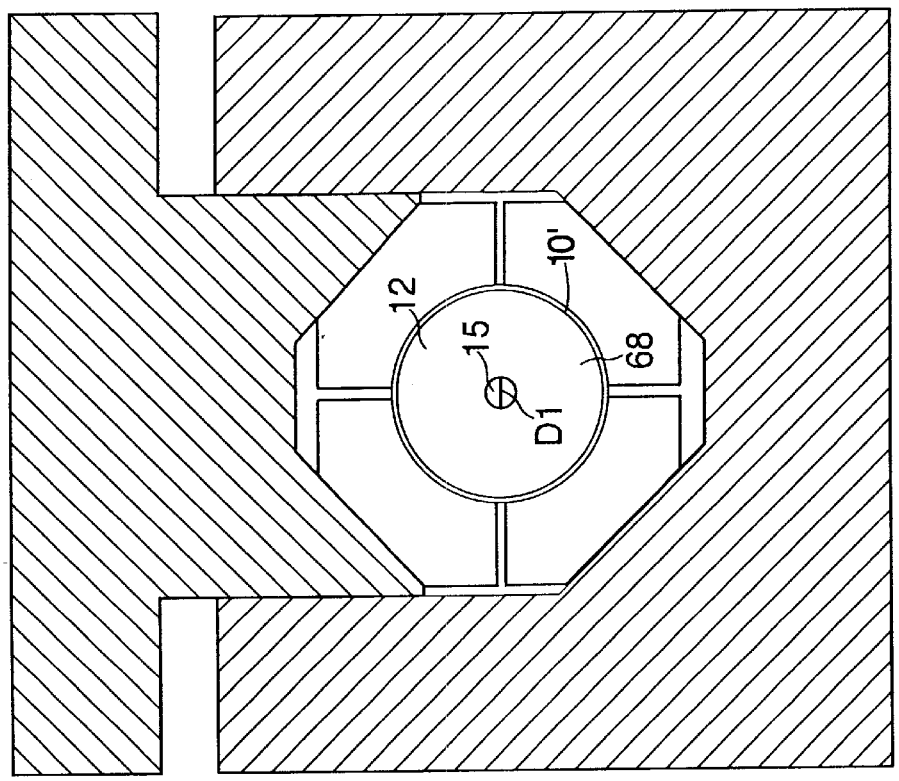
FIG. 15 shows FIG. 13 with a stent crimping sleeve disposed between the crimping elements with the clamping portions and the crimping elements disposed in a first or non-securing position.
Figure 16:
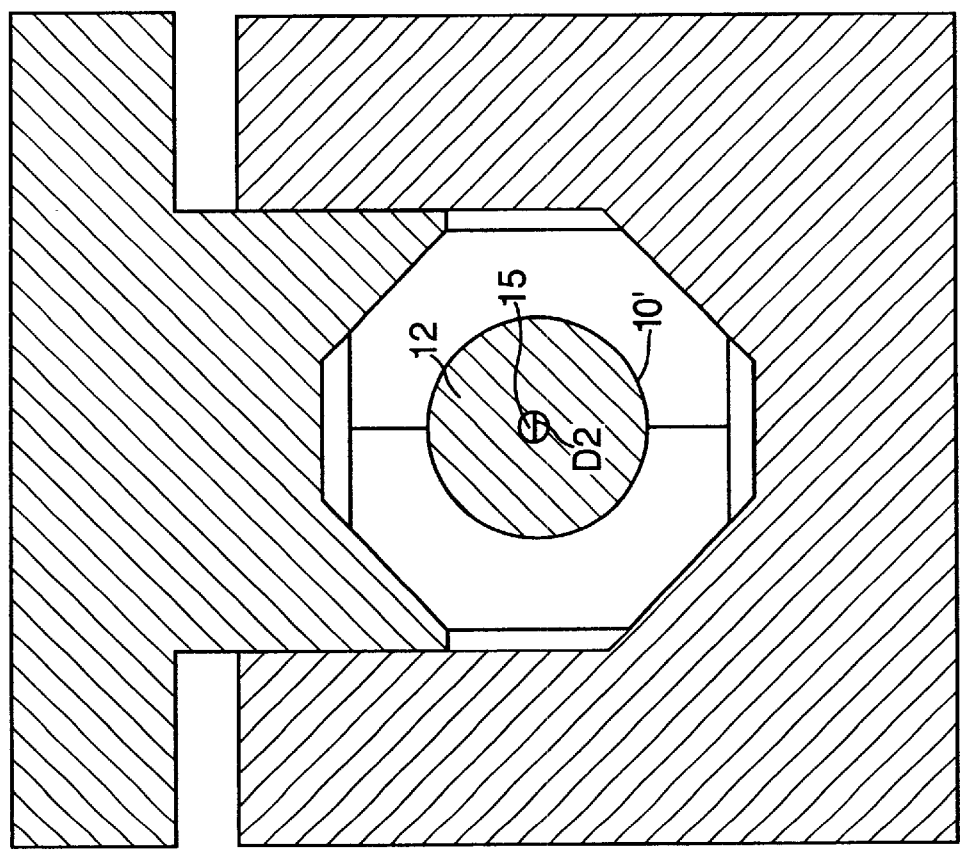
FIG. 16 shows the embodiment shown in FIG. 15 with the clamping portions and the crimping elements disposed in a second or securing position.

FIGS. 15 and 16 show a stent crimping sleeve 12 (previously discussed) disposed in the longitudinal stent crimping sleeve channel 10'. (The stent and balloon catheter have been omitted for clarity.) As shown in FIG. 15, when the first clamping portion 16 and the second clamping portion 18, and the crimping elements 29, 30, 31, and 32 are disposed in the first position, some portions of crimping element contact surfaces 36, 40, 44, and 48 may not be in contact with some portion of the outer surface 13 of the stent crimping sleeve 12 because when the first clamping portion 16, the second clamping portion 18, and the crimping elements 29, 30, 31, and 32 are in the first position, surfaces 36, 40, 44, and 48 do not define a stent crimping sleeve channel 10, having a substantially circular crosssectional diameter. Thus, when the first and second clamping portions and the crimping elements are in the first or non-securing position, gaps 68 may exist between the outer surface 13 of the stent crimping sleeve 12 and crimping element contact surfaces 36, 40, 44, and 48. As shown in FIG. 16, however, when first clamping portion 16, second clamping portion 18, and crimping elements 29, 30, 31, and 32 are disposed in the second or securing position, substantially all of crimping element contact surfaces 36, 40, 44, and 48 are in contact with the external surface 13 of the crimping sleeve 12 because surfaces 36, 40, 44, and 48 are sized and adapted to define a stent crimping sleeve channel 10' having a substantially circular cross-sectional diameter when the first clamping portion 16, the second clamping portion 18, and crimping elements 29, 30, 31, and 32 are disposed in the second position.

As shown in FIG. 15, when the first clamping portion 16, the second clamping portion 18, and crimping elements 29, 30, 31, and 32 are disposed in the first or non-securing position, the stent crimping bore 15 has a substantially circular cross-sectional diameter of D1. As shown in FIG. 16, when the first clamping portion 16, the second clamping portion 18, and crimping elements 29, 30, 31, and 32 are disposed in the second or securing position, the stent crimping bore 15 has a substantially circular cross-sectional diameter D2 that is smaller than D1. Because the stent crimping bore 15 maintains its substantially circular cross-sectional diameter when first clamping portion 16, second clamping portion 18, and crimping elements 29, 30, 31, and 32 are disposed in the second position, the inner surface 14 of the stent crimping sleeve 12 applies substantially uniform pressure to the stent 4 to be crimped mounted on the balloon catheter 1 disposed within the longitudinal stent crimping bore 15 and substantially uniformly crimp and secure the stent 4 to the balloon catheter on which it is mounted with minimal irregular distortion of the stent 4.

Figure 18B:
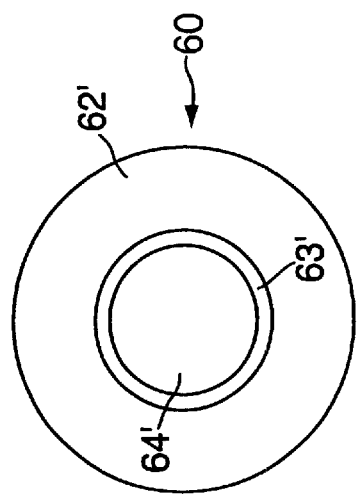
FIG. 18B is an end view of the first catheter protector shown in FIG. 17.
Figure 17:
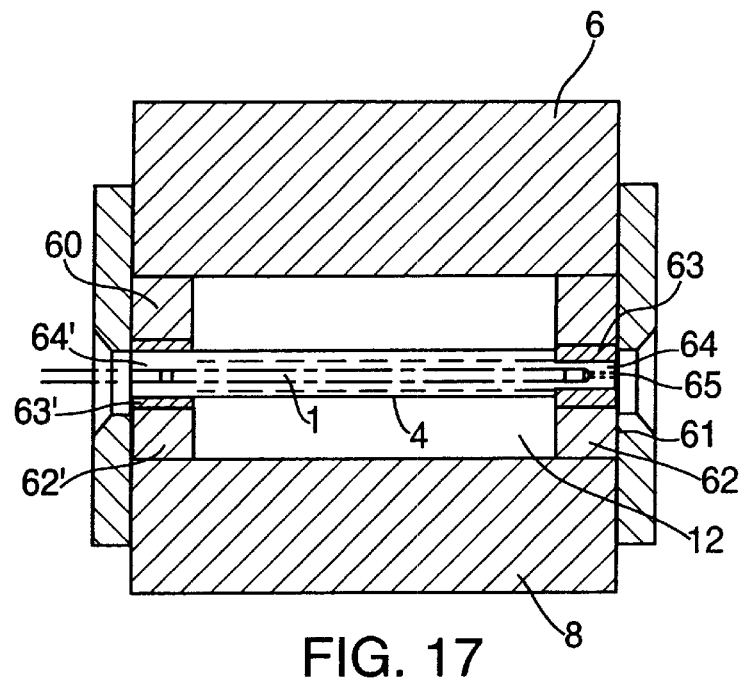
FIG. 17 is a cross-sectional side view of an alternative embodiment of the invention which utilizes a catheter protector and a catheter protector and stent positioners.
Figure 18A:
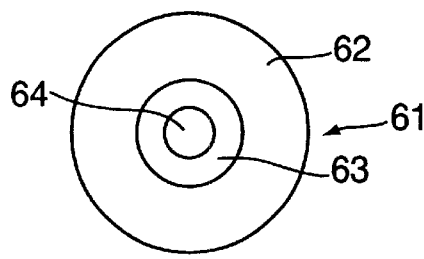
FIG. 18A is an end view of the second catheter protector and stent positioner shown in FIG. 17.
Figure 19:
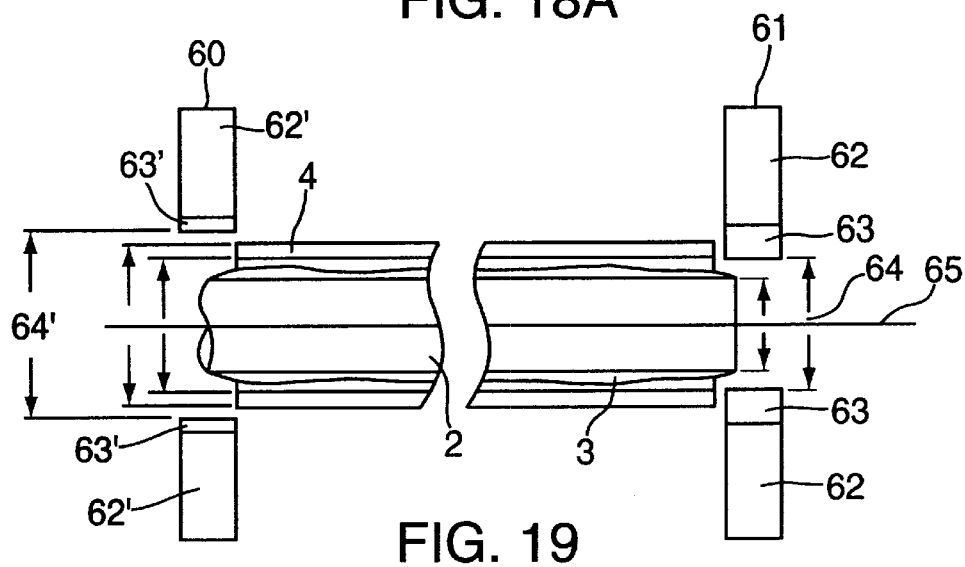
FIG. 19 is an enlarged detailed view of a portion of FIG. 17.

FIGS. 17 to 19 show an alternative embodiment of the invention in which a first catheter protector 60 and a second catheter protector and stent positioner 61 is utilized to protect the catheter shaft and also to limit the movement of the stent along the longitudinal axis of the catheter resulting in more precise placement on the catheter. FIG. 17 is a cross-sectional side view and shows a balloon catheter 1, a stent 4, a guide-wire 65, a first catheter protector 60 and a second catheter protector and stent positioner 61. FIG. 18A is an end view of the second catheter-protector and positioner 61 shown in FIG. 17 and FIG. 18B is an end view of the first catheter protector 60 shown in FIG. 17. As shown in FIG. 18A, the second catheter protector and stent positioner 61 is circular in cross-section and comprises an outer ring 62 of compressible material and an inner ring 63 of substantially non-compressible material. The inner ring 63 is provided with an inner ring aperture 64 having a substantially circular cross-sectional diameter. As shown in FIG. 18B, the first catheter protector 60 is circular in cross-section and comprises an outer ring 62' of compressible material and an inner ring 63' of substantially non-compressible material. The inner ring 63' is provided with an inner ring aperture 64' having a substantially circular cross-sectional diameter. In a preferred embodiment, the substantially compressible material is polyurethane and the substantially non-compressible material is metal.

FIG. 19 is an enlarged view of the second catheter protector and stent positioner 61 and the first catheter protector 60 of FIG. 17. As shown, the inner ring aperture 64 of the substantially non-compressible inner ring 63 of the second catheter protector and positioner 61 is sized sufficiently large so as to permit the catheter 2 to enter into the inner ring aperture 64 and is sized sufficiently small so as to prevent the stent 4 from entering into the inner ring aperture 64. Thus, the inner ring aperture 64 is sized sufficiently small to prevent entrance of the uncrimped stent 4 and is sized sufficiently large to permit entrance of the balloon portion 3 of the catheter 2 into the inner ring aperture 64. Because the inner ring aperture 64 is substantially non-compressible it protects the portions of the catheter 2 and guide-wire 65 disposed within the inner ring aperture 64 of the inner ring 63 during the securing procedure. The substantially non-compressible inner ring 63 also acts as a stop to positively position the stent 4 on the catheter 2. In an especially preferred embodiment, the balloon portion of the catheter has an external diameter of about 0.9 to about 1.2 mm, the inner ring aperture 64 of the second catheter protector and stent positioner 61 has a diameter of about 1.4 mm, the unexpanded and uncrimped stent has an external diameter of about 1.7 to about 1.75 mm and the crimped stent has a diameter of about 1.0 to about 1.1 mm.

As shown in FIGS. 17, 18A, 18B, and 19, the first catheter protector 60 has an inner ring aperture 64' that is larger than the inner ring aperture 64 of the second catheter protector and stent positioner 61. The inner ring aperture 64' is sized large enough to permit the passage of an uncrimped stent through the inner ring aperture 64' and into the longitudinal stent crimping bore of the stent crimping sleeve. In an especially preferred embodiment a diameter of about 1.9 mm to about 2.0 mm is utilized.

In operation, the uncrimped stent is advanced through the inner ring aperture 64' of the first catheter protector 60 and into the longitudinal stent crimping bore until the stent contacts the second catheter protector and stent positioner 61. Because the second catheter protector and stent positioner 61 has an inner ring aperture 64 that is smaller than the diameter of an uncrimped stent and greater than the diameter of the catheter, the catheter positioner and stent positioner 61 serves both to position the stent and to protect the distal end of the catheter. The catheter is then introduced into the longitudinal bore of the stent and the stent is crimped onto the balloon portion of catheter.

After the stent has been crimped on the balloon portion of the catheter, the catheter with the stent crimped on it is withdrawn by pulling the catheter through the inner ring aperture 64' of the first catheter protector 60.

What is claimed is:

1. An apparatus for securing a stent on a balloon catheter, comprising:
   a) a first clamping portion provided with a first clamping portion recess, said first clamping portion recess sized and adapted to receive a stent crimping sleeve;
   b) a second clamping portion provided with a second clamping portion recess, said second clamping portion recess sized and adapted to receive a stent crimping sleeve, said first clamping portion recess and said second clamping portion recess defining a longitudinal stent crimping sleeve channel having a variable cross-sectional diameter, said first and said second clamping portions adapted for movement in a first direction away from each other to a first position and in a second direction toward each other to a second position to selectively impart pressure to a stent crimping sleeve disposed in said longitudinal stent crimping sleeve channel, said clamping portion recesses sized and adapted so that said longitudinal stent crimping sleeve channel has a substantially circular cross-sectional diameter when said first and said second clamping portions are in said second position;
   c) a stent crimping sleeve disposed in said crimping sleeve channel, said sleeve having a first end, a second end, an outer surface, and an inner surface defining a longitudinal stent crimping bore therethrough, said longitudinal stent crimping bore having a selectively variable substantially circular cross-sectional diameter and sized and adapted to receive a balloon catheter with a stent mounted thereon, said stent crimping sleeve further adapted to selectively and substantially uniformly vary said substantially circular cross-sectional diameter of said longitudinal stent crimping bore in response to pressure applied to said external surface of said stent crimping sleeve by said first clamping portion and said second clamping portion when said first clamping portion and said second clamping portion are moved in said second direction.

2. The apparatus of claim 1, wherein said stent crimping sleeve is comprised of polyurethane.

3. The apparatus of claim 2, wherein said longitudinal stent crimping bore has a cross-sectional diameter of about 1.9 mm when said first and said second clamping portions are disposed in said first position.

4. The apparatus of claim 1, further comprising: a first catheter protector disposed at said first end of said stent crimping sleeve and a second catheter protector and stent positioner disposed at said second end of said stent crimping sleeve, said first catheter protector and said second catheter protector and stent positioner each comprising an outer ring of compressible material and an inner ring of substantially non-compressible material, said inner ring of said second catheter protector and stent positioner provided with an aperture sized sufficiently small to prevent entrance of an uncrimped stent and sized sufficiently large to permit entrance of said balloon catheter, said inner ring of said first catheter protector provided with an aperture sized sufficiently large to permit passage of an uncrimped stent.

5. The apparatus of claim 4, wherein said outer ring is comprised of polyurethane and said inner ring is comprised of metal.

6. A method of securing an expandable stent having a longitudinal bore on a balloon catheter, comprising the steps of:
 a) constructing an apparatus comprising: a first clamping portion provided with a first clamping portion recess, said first clamping portion recess sized and adapted to receive a stent crimping sleeve; a second clamping portion provided with a second clamping portion recess, said second clamping portion recess sized and adapted to receive a stent crimping sleeve, said first clamping portion recess and said second clamping portion recess defining a longitudinal stent crimping sleeve channel having a selectively variable cross-sectional diameter, said first and said second clamping portions adapted for movement in a first direction away from each other to a first position and in a second direction toward each other to a second position to selectively impart pressure to a stent crimping sleeve disposed in said longitudinal stent crimping sleeve channel, said clamping portion recesses sized and adapted so that said longitudinal stent crimping sleeve channel has a substantially circular cross-sectional diameter when said first and said second clamping portions are in said second position; a stent crimping sleeve having a first end, a second end, an outer surface, and an inner surface defining a longitudinal stent crimping bore therethrough having a selectively variable substantially circular cross-sectional diameter and sized and adapted to receive an expandable stent, said stent crimping sleeve further adapted to selectively and substantially uniformly vary said substantially circular cross-sectional diameter of said longitudinal stent crimping bore in response to pressure applied to said external surface of said stent crimping sleeve by said first clamping portion and said second clamping portion;
 b) disposing said stent crimping sleeve in said stent crimping sleeve channel;
 c) disposing said stent in said longitudinal stent crimping bore of said stent crimping sleeve;
 d) disposing said catheter in said longitudinal bore of said stent; and
 e) moving said first and said second stent clamping portions from said first position to said second position so as to apply pressure to said external surface of said stent crimping sleeve in an amount sufficient to decrease the substantially circular cross-sectional diameter of said longitudinal stent crimping bore in an amount sufficient for said inner surface of said stent crimping sleeve to impart sufficient pressure to said stent to secure said stent to said balloon catheter.

7. The method of claim 6, further comprising the additional step, prior to step b), of disposing a first catheter protector at said first end of said stent crimping sleeve and a second catheter protector and stent positioner at said second end of said stent crimping sleeve, said first catheter protector and said second catheter protector and positioner each comprising an outer ring of compressible material and an inner ring of substantially non-compressible material, said inner ring of said second catheter protector and stent positioner provided with an aperture sized sufficiently small to prevent entrance of an uncrimped stent and sized sufficiently large to permit entrance of said balloon catheter, said inner ring of said first catheter protector provided with an aperture sized sufficiently large to permit passage of an uncrimped stent.

8. An apparatus for securing a stent having a longitudinal bore on a balloon catheter comprising:
 a) a first clamping portion having a first clamping portion recess and a second clamping portion having a second clamping portion recess, said first and said second clamping portion recesses defining a longitudinal stent crimping element channel with a selectively variable crosssectional diameter, said first and said second clamping portions adapted for movement in a first direction away from each other to a first position and in a second direction toward each other to a second position;
 b) a plurality of crimping elements disposed within said longitudinal stent crimping element channel defining a longitudinal stent crimping sleeve channel having a selectively variable cross-sectional diameter, said plurality of crimping elements adapted for movement in a first direction away from each other to a first position and in a second direction toward each other to a second position; and
 c) a stent crimping sleeve disposed in said longitudinal stent crimping sleeve channel, having a first end, a second end, an outer wall, and an inner wall defining a longitudinal stent crimping bore therethrough having a selectively variable substantially circular cross-sectional diameter, said clamping portions, said crimping elements, and said sleeve adapted and disposed so that when said first clamping portion, said second clamping portion, and said plurality of crimping elements are disposed in said second position, said crimping elements define a longitudinal stent crimping sleeve channel having a substantially circular cross-sectional diameter and said longitudinal stent crimping bore defines a longitudinal bore having a substantially circular cross-sectional diameter.

9. An apparatus for securing a stent having a longitudinal bore on a balloon catheter comprising:
 a) a first clamping portion and a second clamping portion, said first clamping portion provided with a first surface, a second surface and a third surface defining a first clamping portion recess, said second clamping portion provided with a first surface, a second surface, a third surface, a fourth surface and a fifth surface defining a second clamping portion recess, said first and said second clamping portion recesses defining a longitudinal stent crimping element channel with a variable diameter, said first and said second clamping portions adapted for movement in a first direction away from each other to a first position and in a second direction toward each other to a second position;
 b) a first crimping element disposed within said longitudinal stent crimping element channel said first crimping element provided with a first crimping element contact surface, a second crimping element contact surface, a first clamping portion contact surface, and a stent crimping sleeve contact surface;
 c) a second crimping element disposed within said longitudinal stent crimping channel, said second crimping element provided with a first crimping element contact surface, a second crimping element contact surface, a first clamping portion contact surface, and a stent crimping sleeve contact surface;

d) a third crimping element disposed within said longitudinal stent crimping channel, said third crimping element provided with a first crimping element contact surface, a second crimping element contact surface, a second clamping portion contact surface, and a stent crimping sleeve contact surface;

e) a fourth crimping element disposed within said longitudinal stent crimping channel, said fourth crimping element provided with a first crimping element contact surface, a second crimping element contact surface, a second clamping portion contact surface, and a stent crimping sleeve contact surface, said crimping elements adapted for movement in a first direction away from each other to a first position and in a second direction towards each other to a second position, said stent crimping sleeve contact surfaces defining a stent crimping sleeve channel having a variable cross-sectional diameter that is substantially circular when said plurality of crimping elements are disposed in said second position; and f) a stent crimping sleeve disposed in said longitudinal stent crimping sleeve channel, said sleeve having a first end, a second end, an outer wall, and an inner wall defining a longitudinal stent crimping bore therethrough having a selectively variable substantially circular cross-sectional diameter, said clamping portions, said crimping elements, and said sleeve adapted and disposed so that when said first clamping portion and said second clamping portion are in the second position, said crimping sleeve contact surfaces define a stent crimping sleeve channel having a substantially circular cross-sectional diameter and said longitudinal stent crimping bore defines a longitudinal bore having a substantially circular crosssectional diameter.

\* \* \* \* \*